US007356419B1

(12) United States Patent
Culot et al.

(10) Patent No.: US 7,356,419 B1
(45) Date of Patent: Apr. 8, 2008

(54) DERIVING PRODUCT INFORMATION

(75) Inventors: Louis J. Culot, Boston, MA (US); Irwin C. Schreiman, Arlington, MA (US)

(73) Assignee: CambridgeSoft Corporation, Cambridge, MA (US)

( * ) Notice: Subject to any disclaimer, the term of this patent is extended or adjusted under 35 U.S.C. 154(b) by 0 days.

(21) Appl. No.: 09/565,085

(22) Filed: May 5, 2000

(51) Int. Cl.
*G01N 31/00* (2006.01)

(52) U.S. Cl. .................. 702/22; 705/1; 707/3

(58) Field of Classification Search ............ 705/27, 705/22, 28, 1; 702/22, 27; 707/3, 10, 100, 707/102, 104.1; 235/378, 383, 385; 709/203, 709/223, 224, 229
See application file for complete search history.

(56) References Cited

U.S. PATENT DOCUMENTS

| | | | |
|---|---|---|---|
| 4,473,890 A | 9/1984 | Araki et al. | |
| 4,747,059 A | 5/1988 | Hirayama et al. | |
| 4,811,217 A | 3/1989 | Tokizane et al. | |
| 4,908,781 A | 3/1990 | Levinthal et al. | |
| 5,025,388 A | 6/1991 | Cramer, III et al. | |
| 5,157,736 A | 10/1992 | Boyer et al. | |
| 5,249,137 A | 9/1993 | Wilson et al. | |
| 5,345,516 A | 9/1994 | Boyer et al. | |
| 5,379,234 A | 1/1995 | Wilson et al. | |
| 5,418,944 A | 5/1995 | DiPace et al. | |
| 5,424,963 A | 6/1995 | Turner et al. | |
| 5,434,796 A | 7/1995 | Weininger | |
| 5,448,498 A | 9/1995 | Namiki et al. | |
| 5,461,580 A | 10/1995 | Facci et al. | |
| 5,486,995 A | 1/1996 | Krist et al. | |
| 5,577,239 A * | 11/1996 | Moore et al. | 707/3 |
| 5,619,421 A | 4/1997 | Venkataraman et al. | |
| 5,699,268 A | 12/1997 | Schmidt et al. | |
| 5,740,072 A | 4/1998 | Still et al. | |
| 5,740,425 A * | 4/1998 | Povilus | 707/100 |
| 5,778,377 A | 7/1998 | Marlin et al. | |
| 5,841,678 A | 11/1998 | Hasenberg et al. | |
| 5,851,272 A * | 12/1998 | Vicenzi | 106/11 |
| 5,854,992 A | 12/1998 | Shakhnovich et al. | |
| 5,874,564 A | 2/1999 | Ecker et al. | |
| 5,950,192 A * | 9/1999 | Moore et al. | 707/3 |
| 5,956,711 A | 9/1999 | Sullivan et al. | |
| 5,978,804 A | 11/1999 | Dietzman | |

(Continued)

FOREIGN PATENT DOCUMENTS

JP 401161578 6/1989

(Continued)

OTHER PUBLICATIONS

Clinton Wilder, "Net Catalog Sales" Feb. 1, 1999, Information Week; Manhasset, 2 pages.*

(Continued)

*Primary Examiner*—Andrew Joseph Rudy
(74) *Attorney, Agent, or Firm*—Wilmer Cutler Pickering Hale and Dorr LLP

(57) ABSTRACT

A method and a system determine that product information acquired from an electronic catalog includes a product identifier and chemical structure information that is associated with the product identifier. A substance identifier and a quality identifier for a chemical product are derived from product information for a chemical product, and a product identifier for the chemical product is derived from the substance identifier and the quality identifier.

23 Claims, 14 Drawing Sheets

U.S. PATENT DOCUMENTS

| | | | |
|---|---|---|---|
| 5,978,848 A | 11/1999 | Maddalozzo, Jr. et al. | |
| 5,980,096 A | 11/1999 | Thalhammer-Reyero | |
| 6,007,691 A | 12/1999 | Klock, Jr. | |
| 6,014,449 A | 1/2000 | Jacobs et al. | |
| 6,023,659 A | 2/2000 | Seilhamer et al. | |
| 6,023,683 A * | 2/2000 | Johnson et al. | 705/26 |
| 6,038,562 A | 3/2000 | Anjur et al. | |
| 6,055,516 A * | 4/2000 | Johnson et al. | 705/27 |
| 6,061,636 A | 5/2000 | Horlbeck | |
| 6,119,104 A | 9/2000 | Brumbelow et al. | |
| 6,125,383 A | 9/2000 | Glynias et al. | |
| 6,128,582 A | 10/2000 | Wilson et al. | |
| 6,128,619 A | 10/2000 | Fogarasi et al. | |
| 6,178,384 B1 | 1/2001 | Kolossv.ang.ry | |
| 6,185,506 B1 | 2/2001 | Cramer et al. | |
| 6,185,548 B1 | 2/2001 | Schwartz et al. | |
| 6,189,013 B1 | 2/2001 | Maslyn et al. | |
| 6,199,017 B1 | 3/2001 | Tomonaga et al. | |
| 6,219,622 B1 | 4/2001 | Schmidt | |
| 6,226,620 B1 | 5/2001 | Oon | |
| 6,236,989 B1 | 5/2001 | Mandyam et al. | |
| 6,240,374 B1 | 5/2001 | Cramer et al. | |
| 6,246,410 B1 | 6/2001 | Bergeron et al. | |
| 6,256,647 B1 | 7/2001 | Toh et al. | |
| 6,272,472 B1 * | 8/2001 | Danneels et al. | 705/27 |
| 6,295,514 B1 | 9/2001 | Agrafiotis et al. | |
| 6,311,134 B1 * | 10/2001 | Sorenson | 702/22 |
| 6,319,668 B1 * | 11/2001 | Nova et al. | 435/6 |
| 6,323,852 B1 * | 11/2001 | Blower et al. | 345/804 |
| 6,324,522 B2 * | 11/2001 | Peterson et al. | 705/28 |
| 6,326,962 B1 * | 12/2001 | Szabo | 345/348 |
| 6,341,314 B1 | 1/2002 | Doganata et al. | |
| 6,453,064 B1 | 9/2002 | Aikawa et al. | |
| 6,505,172 B1 * | 1/2003 | Johnson et al. | 705/27 |
| 6,519,611 B1 | 2/2003 | Zong et al. | |
| 6,542,903 B2 | 4/2003 | Hull et al. | |
| 6,571,245 B2 | 5/2003 | Huang et al. | |
| 6,584,412 B1 * | 6/2003 | Brecher | 702/27 |
| 6,618,852 B1 | 9/2003 | van Eikeren et al. | |
| 6,631,381 B1 | 10/2003 | Couch et al. | |
| 6,654,736 B1 | 11/2003 | Ellis et al. | |
| 6,675,105 B2 | 1/2004 | Hogarth et al. | |
| 6,678,577 B1 * | 1/2004 | Stylli et al. | 700/218 |
| 6,721,754 B1 | 4/2004 | Hurst et al. | |
| 6,751,615 B2 * | 6/2004 | Nisler et al. | 707/5 |
| 6,871,198 B2 * | 3/2005 | Neal et al. | 707/3 |
| 6,884,394 B1 * | 4/2005 | Hehenberger et al. | 422/55 |
| 2002/0049548 A1 * | 4/2002 | Bunin | 702/32 |
| 2002/0165853 A1 * | 11/2002 | Gogalak | 707/3 |

FOREIGN PATENT DOCUMENTS

| | | | |
|---|---|---|---|
| JP | 401161578 A | * | 6/1999 |

OTHER PUBLICATIONS

PR Newswire; New York, "Fisher Scientific Adopts Standards; New Electronic Commerce Web Site Among the First to Embrac' Open Buying on the Internet Standards" Feb. 9, 1998, 2 pages.*

Greg R. Notess, "Offspring of OPACSs: Local databases on the net" Jun. 1993, Database; Weston, 4 pages.*

PR Newswire, Judy Hunter, "CAS and Dialog agree to publish new standard," New York, Sep. 29, 1994, Sec. 1, p. 1 (two pages total).*

Information Today, "ISI devleops electronic Index Chemicus," Medford, May 1993, vol. 10, Iss. 5, p. 64, 1 pg. (two pages tota.*

CS Chemfinder, Searching and Information Integration, The ChemFinder WebServer: Indexing Chemical Data on the Internet. 1999, 12 pages.*

CambridgeSoft News, "Inventory Tracking and ChemOffice: CIS Pro Chemical Inventory Package Contects with CS ChemOffice," 2 pages, Aug. 24, 1998.*

CambridgeSoft News, "ChemACX Chemical Database: Search Over 100 Leading Catalogs on Your Desktop or on the WWW," 3 pages, Jan. 18, 1999.*

Anonymous, "Databases Added to ChemWeb", *Information Today*, 2 pages, May 1998.

Balasubramanian, K.J., "Computer Perception of Molecular Symmetry", *J. Chem. Inf. Comput. Sci.*, vol. 35, pp. 761-770, 1995.

Balducci, R. et al., "Efficient Exact Solution of the Ring Perception Problem", *J. Chem. Inf. Comut. Sci.*, vol. 34, pp. 822-831, 1994.

Barnard, J.M., "Substructure Searching Methods: Old and New", *J. Chem. Inf. Comput. Sci.*, vol. 33, pp. 532-538, 1993.

Barsamiam, S.T. et al., "Dielectric phenomenon of living matter", *IEEE Transactions of Dielectrics and Electrical Insultation*, vol. 4, No. 5, pp. 629-643, Oct. 1997.

Bauer, J. et al., "IGOR and RAIN—The First Mathematically Based Multi-Purpose Problem-Solving Computer Programs for Chemistry and Their Use as Generators of Constitutional Formulas", *Informal Commun. Math. Chem. (MATCH)*, No. 27, pp. 31-47, 1992.

Bayada, D.M. et al., "An Algorithm for the Multiple Common Subgraph Problem", *J. Chem. Inf. Comput. Sci.*, vol. 32, pp. 680-685, 1992.

Benecke, C. et al., "MOLGEN, a generator of connectivity isomers and stereoisomers for molecular structure elucidation", *Anal. Chim. Acta*, vol. 314, pp. 141-147, 1995.

Bertrand, A. et al., "DESMOL: a Subroutine for the Generation of Molecular Structures with Stereochemical Information from Connectivity Data", *J. Chem. Res. (S)*, p. 158, 1994.

Brecher, The ChemFInder WebServer: Indexing Chemical Data on the Internet:, *CHIMIA*, vol. 52, pp. 658-661, 1998.

Business Editors/Health & Medical Writers, "Janssen Selects MDL's ISIS, Relational Chemical Gateway as Informatics Foundation for High Throughout Discovery", 3 pages, Dec. 2, 1998.

Cambridge Scientific Computing, Inc., "Chem3D the Molecular Modeling System", pp. 1-337, 1990.

CambridgeSoft Solutions Products Overview, 28 pages describing their product lines.

Carhart, R.E., "A Model-Based Approach to the Teletype Printing of Chemical Structures", *J. Chem. Inf. Comput. Sci.*, vol. 16, No. 2, pp. 82-88, 1976.

Casey et al., "Optical recognition of chemical graphics", *Proceedings of the Second International Conference on Document Analysis and Recognition*, pp. 627-631, Oct. 20-22, 1993.

Cash, "A Simple Means of Computing the Kekule Structure Count for Toroidal Polyhex Fullerenes", *J. Chem. Inf. Comput. Sci.*, vol. 38, No. 1, pp. 58-61, 1998.

ChemDraw Chemical Structure Drawing Standard, *User's Guide*, CS Chem3D 4.0 for Windows and MacIntosh, CambridgeSoft Corporation, 1986-1997.

ChemDraw Chemical Structure Drawing Standard, *User's Guide*, CS ChemDraw Pro Version 4.0 for Microsoft Windows and Apple MacIntosh, CambridgeSoft Corporation, 1986-1996.

ChemDraw Chemical Structure Drawing Standard, *User's Guide*, CS ChemDraw 4.5 for Windows and MacIntosh, CambridgeSoft Corporation, 1986-1997.

ChemDraw: Chemical Structure Drawing Standard (Publ. CambridgeSoft Corp.), pp. 68-69.

ChemDraw and Chem3D version history, 8 pages of version history dating back to 1985.

Cheminovation Software, "Chemistry 4-D Draw", *User's Guide*, pp. 1-61, 1997.

Chem3D Molecular Modeling and Analysis, *User's Guide*, CS Chem 3D 4.0 for Windows and MacIntosh, CambridgeSoft Corporation, 1986-1997.

Chem3D The Molecular Modeling System Version 3.0, Cambridge Scientific Computing, Inc., 1986-1990.

Cooke-Fox et al., "Computer Translation of IUPAC Systematic Organic Chemical Nomenclature. 1.Introduction and Background to a Grammar-Based Approach", *J. Chem. Inf. Comput. Sci.*, vol. 29, pp. 101-105, 1989.

Cooke-Fox et al., "Computer Translation of of IUPAC Systematic Organic Chemical Nomenclature.2.Development of a Formal Grammar", *J. Chem. Inf. Comput. Sci..*, vol. 29, pp. 106-112, 1989.

Cooke-Fox et al., "Computer Translation of IUPAC Systematic Organic Chemical Nomenclature.3.Syntax Analysis and Semantic Processing", *J. Chem. Inf. Comput. Sci.*, vol. 29, pp. 112-118, 1989.
Cooke-Fox et al., "Computer Translation of IUPAC Systematic Organic Chemical Nomenclature.4.Concise Connection Tables to Structure Diagrams", *J. Chem. Inf. Comput. Sci.*, vol. 30, pp. 122-127, 1990.
Cooke-Fox et al., "Computer Translation of IUPAC SYstematic Organic Chemical Nomenclature.5.Steroid Nomenclature", *J. Chem. Inf. Comput. Sc.*, vol. 30, pp. 128-132, 1990.
Cooke-Fox et al., "From names to diagrams—by computer", *Chemistry in Britain*, pp. 467-471, 1985.
CRC Handbook of Chemistry and Physics, Student Edition, 76th Edition, Section 2, pp. 2-22 through 2-26, 1996-1996.
CS ChemDraw for Apple MacIntosh, *Quick Reference*, CambridgeSoft Corp., 1986-1996.
CS ChemFinder Searching and Information Integration, *User's Guide*, CS ChemFinder Pro and CS ChemFinder, Version 2.0 for Apple MacIntosh, CambridgeSoft Corporation, 1991-1995.
CSC ChemDraw Chemical Structure Drawing Standard, *User's Guide*, CSC ChemDraw and CSC ChemDraw Plus Version 3.0 for Apple MacIntosh, CambridgeSoft Corporation, 1986-1996.
CSC Chemical Finder Chemical Information Management, *User's Guide*, Version 1.0 for Apple MacIntosh, Cambridge Scientific Computing, Inc., 1991-1992.
CSC Chem3D Molecular Modeling and Analysis, *Tutorial*, CSC Chem3D and CSC Chem 3D Plus, Version 3.1 for Apple MacIntosh, Cambridge Scientific Computing, Inc., 1986-1993.
Dalby, J. et al., "Description of Several Chemical Structure File Formats Used by Computer Programs Developced at Molecuar Design Limited", *J. Chem. Inf. Comput. Sci.*, vol. 32, pp. 244-255, 1992.
Dittmar, P.G. et al., "An Algorithmic Computer Graphics Program for Generating Chemical Structure Diagrams", *J. Chem. Inf. Comput. Sci.*, vol. 17, No. 3, pp. 186-192, 1977.
Downs, G.M. et al., "Review of Ring Perception Algorithms for Chemical Graphs", *J. Chem. Inf. Comput. Sci.*, vol. 29, pp. 172-187, 1989.
Ertl, P. et al., "WWW-Based Chemical Information System", *Journal of Molecular Structure (Theochem)*, vol. 449, p. 113-129, Dec. 8, 1997.
Fan et al., "Detection of constitutionally equivalent sites from a connection table", *J. Chem. Inf. Comput. Sci.*, VVOl. 36, pp. 654-659, 1996.
Figueras, J. et al., "Automorphism and Equivalence Classes", *J. Chem. Inf. Comput. Sci.*, vol. 32, pp. 153-157, 1992.
Figueras, J., "Ring Perception Using Breadth-First Search", *J. Chem. Inf. Comput. Sci.*, vol. 36, p. 986-991, 1996.
Frerejacque, M., "No. 108—Condensation d'une molecule organique", *Bull. Soc. Chim. Fr.*, (*Memories*), vol. 5, pp. 1008-1011, 1939.
Glendening et al., "Natural Resonance Theory: I. General Formalism", *Journal of Computational Chemistry*, vol. 19, No. 6, pp. 593-609, Apr. 30, 1998.
Gothe, S.A. et al., "Computer-Assisted Mechanistic Evaluation of Organic Reactions. 22. The Generation and Use of Three-Dimensional Structures", *J. Org. Chem.*, vol. 58, pp. 5081-5094, 1993.
Graovac et al., "Kekule Index for Valence Bond Structures of Conjugated Polycyclic Systems", *Journal of the American Chemical Society*, vol. 95, No. 19, pp. 6267-6273, 1973.
Helson et al., "Computer-Assisted Mechanisitic Evaluation of Organic Reactions. 25. Structure Diagram Positioning", *J. Chem. Inf. Comput. Sci.*, vol. 34, p. 962, 1993.
Helson, "Simulation of Carbene Chemistry and Other Problems in Computer Assisted Organic Synthesis", *Thesis*, Purdue University, 1993.
Helson, "Structure Diagram Generation", *Reviews in Computational Chemistry*, vol. 13, Ch. 6, pp. 313-398, 1999.
Hu et al., "Computer perception of topological symmetry by all-paths algorithm", Abstract, *Chemometrics and Intelligent Laboratory Systems*, 45, pp. 317-322, Jan. 1999.
Hyde, E. et al., "Structure Display", *J. Chem. Doc.*, vol. 8, No. 3., pp. 138-146, 1968.

Ihde, A., "The Development of Modern Chemistry", The University of Wisconsin, Dover Publications, pp. 305-309, NY, 1984.
Ihlenfeldt, W.W. et al., "Augmenting Connectivity Information by Compound Name Parsing: Automatic Assignment of Stereochemistry and Isotope Labeling", *J. Chem. Inf. Comput. Sci.*, vol. 35, pp. 663-674, 1995.
Ihlenfeldt, W.D. et al., "Beyond the Hyperative Molecule: Search, Salvage and Visualization of Chemical Information from the Internt", *Pacific Symposium on Biocomputing '96*, vol. SYMP.1, pp. 384-398, Jan. 3, 1996.
Ihlenfeldt et al., *Journal of Chemical Information and Computer Sciences*, vol. 35, No. 4, Jul.-Aug. 1995 (Abstract Only).
Jorgensen, W.L. et al., "CAMEO: a program for the logical prediction of the products of organic reactions", *Pure App.l. Chem.*, vol. 62, pp. 1921-1932, 1990.
Judson, R., "Genetic Algorithms and Their Use in Chemistry", *Reviews of Computational Chemistry*, Ch. 1, vol. 10, pp. 1-73, 1997.
Kirby et al., "Computer Translation of IUPAC Systematic Organic Chemical Nomenclature. 6. (Semi) Automatic Name Correction", *J. Chem. Inf. Comput. Sci.*, vol. 31, pp. 153-160, 1991.
Lieth, C.v.d. et al., "RINGS—a general program to build ring systems", *J. Mol. Graphics*, vol. 2, pp. 117-123, 1984.
Lipkowitz et al., "Chapter 6. Structure Diagram Generation", *Reviews in Computational Chemistry*, vol. 13, pp. 313-398, 1999.
Molchanova, M.S. et al., "Computer Generation of Molecular Structures by the SMOG Program", *J. Chem. Inf. Comput. Sci.*, vol. 36, pp. 888-899, 1996.
Morikawa, "Enumeration of Kekule Structures in Polyradical Polyhexes", *Computers Chem.*, vol. 20, No. 2, pp. 159-165, 1996.
Morrison et al., *Organic Chemistry, Third Edition*, pp. 261 and 1011, Copyright 1973.
Morrison et al., *Organic Chemistry, Third Edition*, p. 324, Copyright 1973.
Morrison et al., "Structure and Properties", *Organic Chemistry, Third Edition*, pp. 4-8, Copyright 1973.
New Riverside University Dictionary, Riverside Publishing Company, Boston, MA, p. 783, 1984.
Rayner, J.D. et al., "A Concise Connection Table Based on Systematic Nomenclatural Terms", *J. Mol. Graphics*, vol. 1, pp. 108-111, 1983.
Razinger et al., "Graph Automorphism Perception Algorithms in Computer-Enhanced Structure Elucidation", *J. Chem. Inf. Comput. Sci..*, vol. 33, pp. 197-201, 1993.
Registry (Dictionary Searching) STN Database Summary Sheet, Revised, Chemical Abstracts Services, pp. 1-10, Mar. 1997.
Rubenstein, S., "ChemDraw Professional Desktop Publishing for Chemists", Version 2.0 Cambridge Scientific Computing, Inc., 1985-1988.
Ruiz et al., "Error Detection, Recovery, and Repair in the Translation of Inorganic Nomenclatures. 1. A Study of the Problem", *J. Chem. Inf. Comput. Sci..*, vol. 36, No. 1, pp. 16-24, 1996.
Rusinko, A. et al., "Using CONCORD to Construct a Large Database of Three-Dimensional Coordinates from Connection Tables", *J. Chem. Inf. Comput. Sci.*, vol. 29, p. 251-255, 1989.
Sadowski, J. et al., "Comparison of Automatic Three-Dimensional Model Builders Using 639 X-ray Structures", *J. Chem. Inf. Comput. Sci.*, vol. 34, p. 1000-1008, 1995.
Shelley, C.A. et al., "An approach to the assignment of canonical connection tables and topological symmetry perception", *J. Chem. Inf. Comput. Sci.*, vol. 19, No. 4, pp. 247-250, 1979.
Shelley, C.A., "Heuristic Approach for Displaying Chemical Structures", *J. Chem. Inf. Comput. Sci.*, vol. 23, pp. 61-65, 1983.
Shmueli, U., "Simple and efficient approach to preparation of molecular drawings", *J. Mol. Graphics*, vol. 2, pp. 111-112, 1984.
Stillwell, "Computer Translation of Systematic Chemical Nomenclature to Structural Formulas—Steroids", *Journal of Chemical Documentation*, vol. 13, No. 3, pp. 107-109, 1973.
Thomson, L.G. et al., "Organic Search and Display Using a Connectivity Matrix Derived from Wiswesser Notation", *J. Chem. Doc.*, vol. 7, pp. 204-209, Nov. 1967.
Vander Stouw et al., "Automated Conversion of Chemical Substasnces Names to Atom-Bond Connection Tables", *Journal of Chemical Documentation*, vol. 14, No. 4, pp. 185-193, 1974.

Vander Stouw et al., "Procedures for Converting Systematic Names of Organic Compounds into Atom-Bond Connection Tables", *Journal of Chemical Documentation*, vol. 7, No. 3, pp. 165-169, 1967.

Weininger, D., "Smiles. 3. Depict. Graphical Depiction of Chemical Structures", *J. Chem. Inf. Comput. Sci.*, vol. 30, pp. 237-243, 1990.

Weininger, D., "SMILES, a Chemical Language and Information System. 1. Introduction to Methodology and Encoding Rules", *J. Chem. Inf. Comput. Sci.*, vol. 28, pp. 31-36,1988.

Wipke, T., "AIMB: Analogy and Intelligence in Model Building. System Description and Performance Characteristics", *Computer Representation and Manipulation of Chemical Information*, pp. 147-174, Wipke et al. editors, Krieger, NY, 1981.

Wipke, W. T. et al., "Computer-Assisted Three-Dimensional Synthetic Analysis", *Tet. Comput. Method.*, vol. 1, pp. 147-174, 1988.

www.cambridgesoft.com/services/history.cfm?FID=1, printed Apr. 9, 2004, 7 pages.

www.cambridgesoft.com/services/history.cfm?FID=2, printed Apr. 9, 2004, 6 pages.

www.cambridgesoft.com/services/history.cfm?FID=3, printed Apr. 9, 2004, 3 pages.

www.cambridgesoft.com/services/history/cfm?FID=4, printed Apr. 9, 2004, 2 pages.

Zimmerman, B.L., Thesis, University of Pennsylvania, 1971.

Zipple, M. et al., "Spektren—A Computer System for the Identification and Structure Elucidation of Organic Compounds", *Anal. Chim Acta*, vol. 140, pp. 123-142, 1982.

Gelin, B. R. et al., "Inventory Tracking and ChemOffice: CIS Pro Chemical Inventory Package Connects with CS ChemOffice," CambridgeSoft News, Press Release, Aug. 24, 1998, 2 pages.

Gelin, B. R., "ChemACX Chemical Database: Search Over 100 Leading Catalogs on your Desktop or on the WWW," CambridgeSoft News, Press Release, Jan. 18, 1999, 3 pages.

Gelin, B.R., "CS ChemInfo WebServer: Subscription Services Offer WWW Substructure Searching," CambridgeSoft News, Press Release, Aug. 24, 1998, 2 pages.

\* cited by examiner

| 62 ↱ CATALOG ITEM NUMBER | 64 ↱ PRODUCT NAME | 66 ↱ CHEMICAL NAME | 68 ↱ CAS NUMBER | 70 ↱ SUPPLIER | 72 ↱ PACKAGE TYPE | 74 ↱ STRUCTURE | 76 ↱ PRICE |
|---|---|---|---|---|---|---|---|
| 22 | BAKING SODA BAKERY GRADE | SODIUM BICARBONATE | Z9999999 | 319 | 555 | 12345 | 7.20 |

1. Substance Table

| | | | |
    |---|---|---|---|
    | 1.1. | CAS | Text | 50-02-2 |
    | 1.2. | FEMA | Text | 2349 |
    | 1.3. | MOL_ID | Long Integer | 12345 |
    | 1.4. | SynonymID | Long Integer | 12345 |
    | 1.5. | DateCreated | Date | 05/29/1998 4:25:59 PM |
    | 1.6. | SupplierName | Text | My Chemical Company, Inc. |
    | 1.7. | SupplierID | Long Inreger | 23 |
    | 1.8. | ACX_ID | Text | X1011594-5 |
    | 1.9. | NumProducts | Long Integer | 23 |
    | 1.10. | NumSuppliers | Long Integer | 5 |
    | 1.11. | CsNum | Long Integer | 12345 |

2. Synonym Table

| | | | |
    |---|---|---|---|
    | 2.1. | SynonymID | Long Integer | 12345 |
    | 2.2. | Name | Text | Ethanol |
    | 2.3. | SynonymType | Text | Chemical |
    | 2.4. | DateCreated | Date | 05/29/1998 4:25:59 PM |
    | 2.5. | SupplierName | Text | My Chemical Company, Inc. |
    | 2.6. | SupplierID | Long Integer | 23 |
    | 2.7. | CsNum | Long Integer | 12345 |

3. Product Table

| | | | |
    |---|---|---|---|
    | 3.1. | ProductID | Long Integer | 12345 |
    | 3.2. | ProdName | Text | Ethyl Alcohol |
    | 3.3. | ProdDescrip | Text | Absolute |
    | 3.4. | CatalogNum | Text | E-101 |
    | 3.5. | DateCreated | Text | 05/29/1998 4:25:59 PM |
    | 3.6. | SupplierID | Long Integer | 23 |
    | 3.7. | MOL_ID | Long Integer | 12345 |
    | 3.8. | Picture | Text | graphics.camsoft.com/12345.gif |
    | 3.9. | ExtendedDescription | Memo | <b>[MOPC 315]</b><br>This myeloma proteins are purified from ascites by a combination of salt precipitation, ion exchange and bioaffinity chromatography. Purified proteins are dialyzed into 0.02M Tris,0.14M sodium chloride, pH 8.1. Product is adjusted to 1.0 mg/ml, filtered, vialed, and stored FROZEN AT -70°C. Product are shipped on dry ice. |
    | 3.10. | ACX_ID | Text | X1011594-5 |
    | 3.11. | CSNum | Long Integer | 12345 |

4. Property Alpha Table

| | | | |
    |---|---|---|---|
    | 4.1. | Property AlphaID | Long Integer | 415 |
    | 4.2. | PropertyClassAlphaID | Long Integer | 12 |
    | 4.3. | Value | Text | 123-125°C |
    | 4.4. | ProductID | Long Integer | 12345 |

5. PropertyClassAlpha Table

| | | | |
    |---|---|---|---|
    | 5.1. | PropertyClassAlphaID | Long Integer | 12 |
    | 5.2. | Value | Text | Boiling Point |

FIG. 13A

6. Package Table

| | | |
|---|---|---|
| 6.1. PackageID | Long Integer | 12345 |
| 6.2. Size | Text | 1 L |
| 6.3. Container | Text | safety coated glass bottle |
| 6.4. Catalog2Num | Date | E101-1000 |
| 6.5. PRICE | Text | 50.00 |
| 6.6. DISCPRICE | Double | 47.50 |
| 6.7. SAVINGS | Double | 2.50 |
| 6.8. Currency | Text | US Dollars |
| 6.9. CurrencySymbol | Text | $ |
| 6.10. PriceURL | Text | prices.camsoft.com/PID=12345/ |
| 6.11. ProductID | Long Integer | 12345 |
| 6.12. DateCreated | Date | 05/29/1998 4:25:59 PM |
| 6.13. SupplierName | Text | My Chemical Company, Inc. |
| 6.14. SupplierID | Long Integer | 23 |

7. Price Table

| | | |
|---|---|---|
| 7.1. Price | Text | 50.00 |
| 7.2. Currency | Text | US Dollars |
| 7.3. CurrencySymbol | Text | $ |
| 7.4. Discount | Number | 15% |
| 7.5. URL | Text | prices.camsoft.com/PID=12345/ |
| 7.6. Comment | Text | Merck discount |
| 7.7. PackageID | Long Integer | 12345 |

8. Supplier Table

| | | |
|---|---|---|
| 8.1. SupplierID | Long Integer | 23 |
| 8.2. Name | Text | My Chemical Company, Inc. |
| 8.3. LogoPath | Text | graphics.camsoft.com/MyChemLogo.gif/ |
| 8.4. Logo | Binary Large Object | |

9. SupplierPhoneID Table

| | | |
|---|---|---|
| 9.1. SupplierPhoneID | Long Integer | 17 |
| 9.2. Country Code | Text | 1 |
| 9.3. AreaCode | Text | 617 |
| 9.4. PhoneNum | Text | 555-5555 |
| 9.5. Type | Text | Fax |
| 9.6. Location | Text | USA |
| 9.7. SupplierID | Long Integer | 23 |

10. SupplierAddr Table

| | | |
|---|---|---|
| 10.1. SupplierAddr ID | Long Integer | 15 |
| 10.2. Addr1 | Text | 1234 Main Street |
| 10.3. Addr2 | Text | Suite 243 |
| 10.4. City | Text | Cambridge |
| 10.5. State | Text | MA |
| 10.6. Code | Text | 02140 |
| 10.7. Countrt | Text | USA |
| 10.8. Type | Text | email |
| 10.9. SupplierID | Long Integer | 23 |

FIG. 13B

DERIVING PRODUCT INFORMATION

BACKGROUND OF THE INVENTION

This application relates to deriving product information.

A product that is specified by a customer is sometimes not available, at least not within a time period specified by the customer. As a result, the customer may be interested in determining the availability of an acceptable substitute for the specified product. However, determining the acceptability of candidate substitutes can present a significant challenge, particularly if information that is necessary to the acceptability determination is unavailable or incomprehensible to the person who is in charge of acquiring the acceptable substitute.

For example, in an organization that uses research chemicals, a scientist may specify a research chemical product by brand name to a purchasing agent. In such a case, if the specified brand name product is not available, the purchasing agent may not be able to find a substitute that is acceptable to the scientist without involving the scientist in a time consuming trial and error exercise that reduces the productivity of the purchasing agent and the scientist. In particular, if the research chemical is available in different grades or purities from different manufacturers, and in different containers, it may be difficult to determine, from the way in which the scientist originally specified the research chemical, whether a candidate substitute has characteristics that are suitable for the purpose for which the specified product is sought.

In a case in which the specified product is a research chemical, the specification may include a Chemical Abstracts Service registry number ("CAS number") number, which identifies a substance.

SUMMARY OF THE INVENTION

Methods and systems are provided for deriving product information. A standardized products database is derived from product information that is provided in different formats in multiple electronic catalogs from multiple sources. The product information is standardized and is linked in the database to allow an end user to determine a set of differently sourced products that meet a set of criteria, such as substance and package criteria. A compact, standardized, descriptive product identifier is derived from the product information in the catalogs or the database.

Different aspects of the invention allow one or more of the following. A database of research chemical products can be provided that allows an end user to produce reports listing chemical products of the same substance from different suppliers. Product information from different sources can be consolidated in an effective way with little input from an end user. Products that are known by different names, such as some chemical substances, can be found by searching under one or other subset of the names. Shopping efficiency can be increased by allowing an end user to view characteristics of different suppliers' chemical products side by side, and by allowing indications of important characteristics of a desired chemical product to be communicated to a purchasing agent or a seller unintrusively in a compact, universal format that can be interpreted accurately by a computer. A quality category to which a product belongs may be determined by reference to an identification number for the product.

Other features and advantages will become apparent from the following description, including the drawings, and from the claims.

BRIEF DESCRIPTION OF THE DRAWINGS

FIGS. 5, 7, 8, 12 and 13A-13B are illustrations of computer data.

FIGS. 9-11 are illustrations of output produced by software.

DETAILED DESCRIPTION

Figure 1:
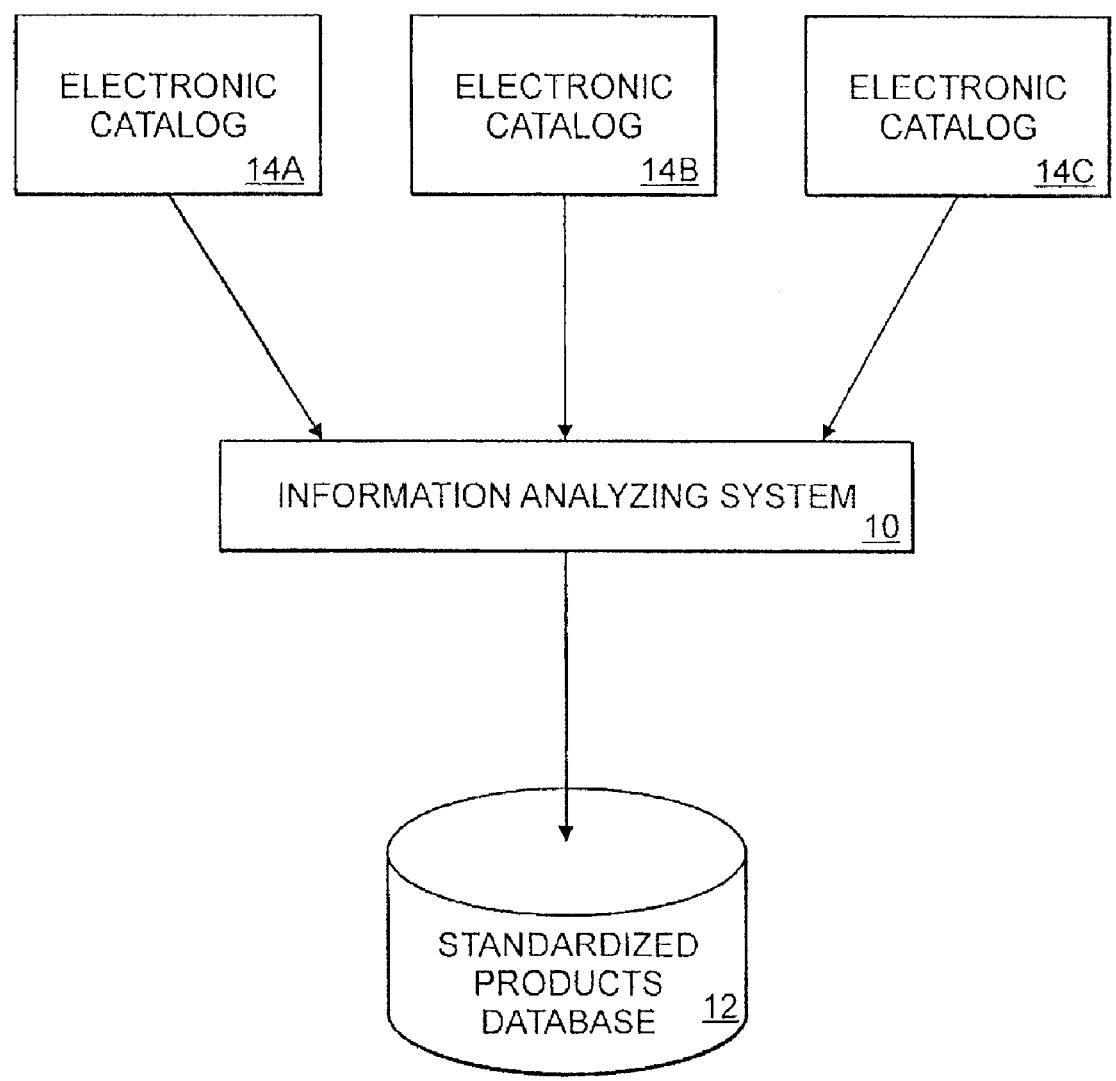
FIGS. 1 and 3-4 are block diagrams of computer-based systems.

FIG. 1 illustrates an information analyzing system 10 by which a standardized products database 12 is derived from multiple, differently organized electronic catalogs of product information 14A-14C. The standardized products database stores information about products' characteristics in a uniform way so that it may be readily determined which products have similar characteristics, which can facilitate finding a product that is an acceptable substitute for another product for a particular purpose.

Figure 2:
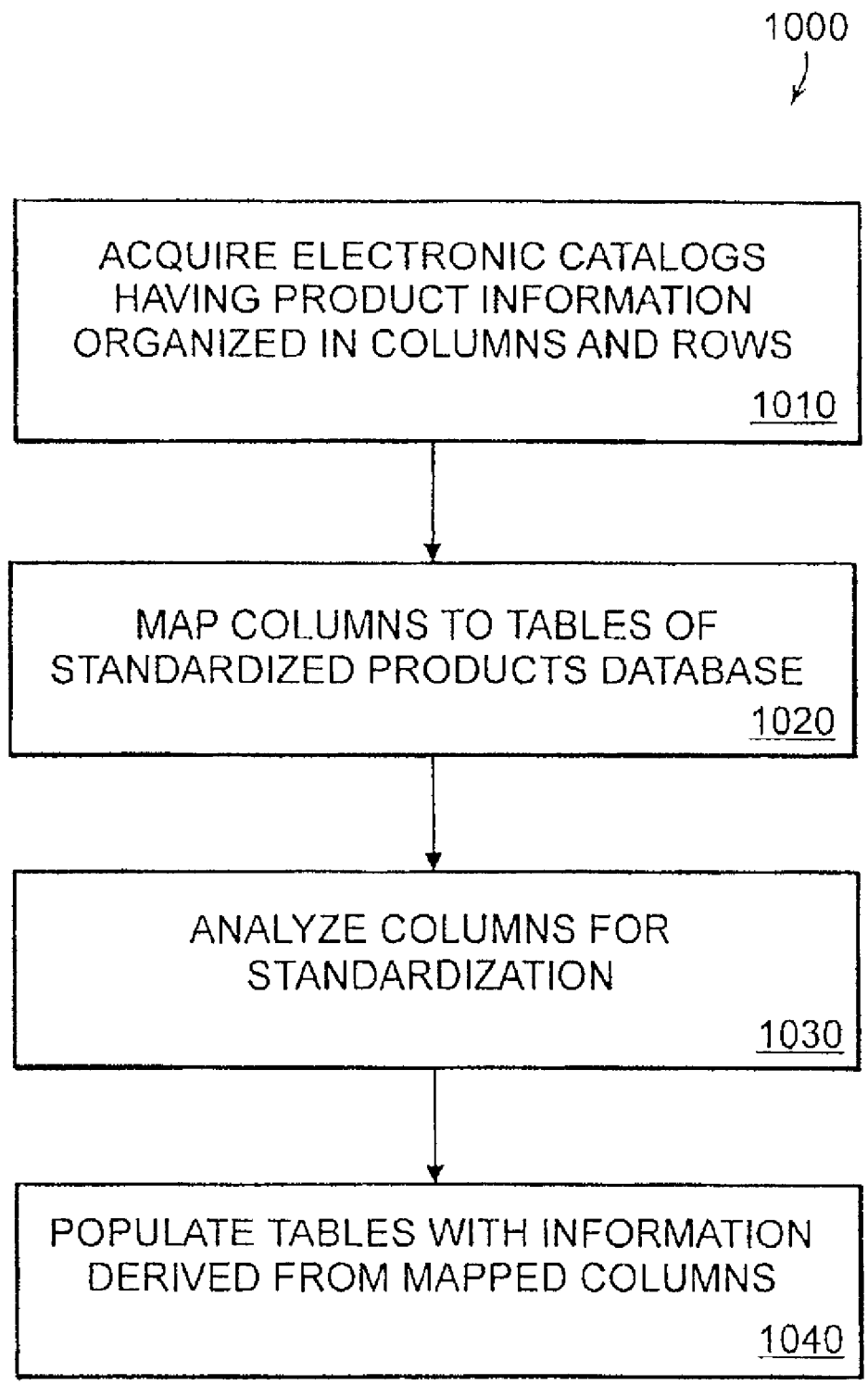
FIGS. 2 and 6 are flow diagrams of computer-based procedures.
Figure 3:
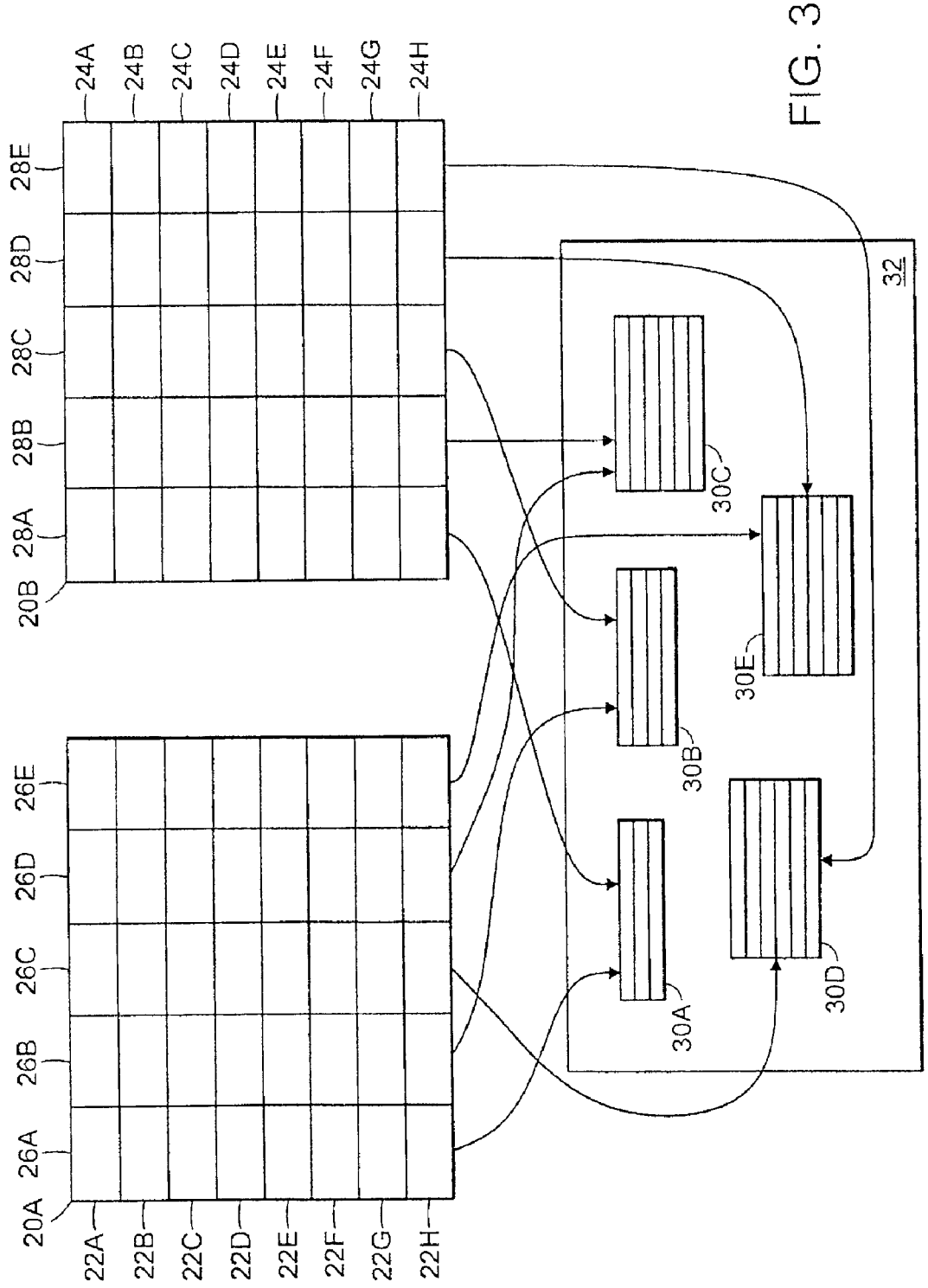

With respect to procedure 1000 (FIG. 2), in a specific implementation (FIG. 3), differently organized electronic catalogs are acquired in the form of respective spreadsheet files 20A, 20B having product information organized in respective rows of products 22A-22H, 24A-24H and columns of product characteristics 26A-26E, 28A-28E (step 1010). One or more of the columns are mapped to one or more tables 30A-30E of a standardized products database 32 (step 1020). Information in one or more of the mapped columns is analyzed for standardization (step 1030). The tables are populated with information derived from the mapped columns (step 1040).

Figure 4:
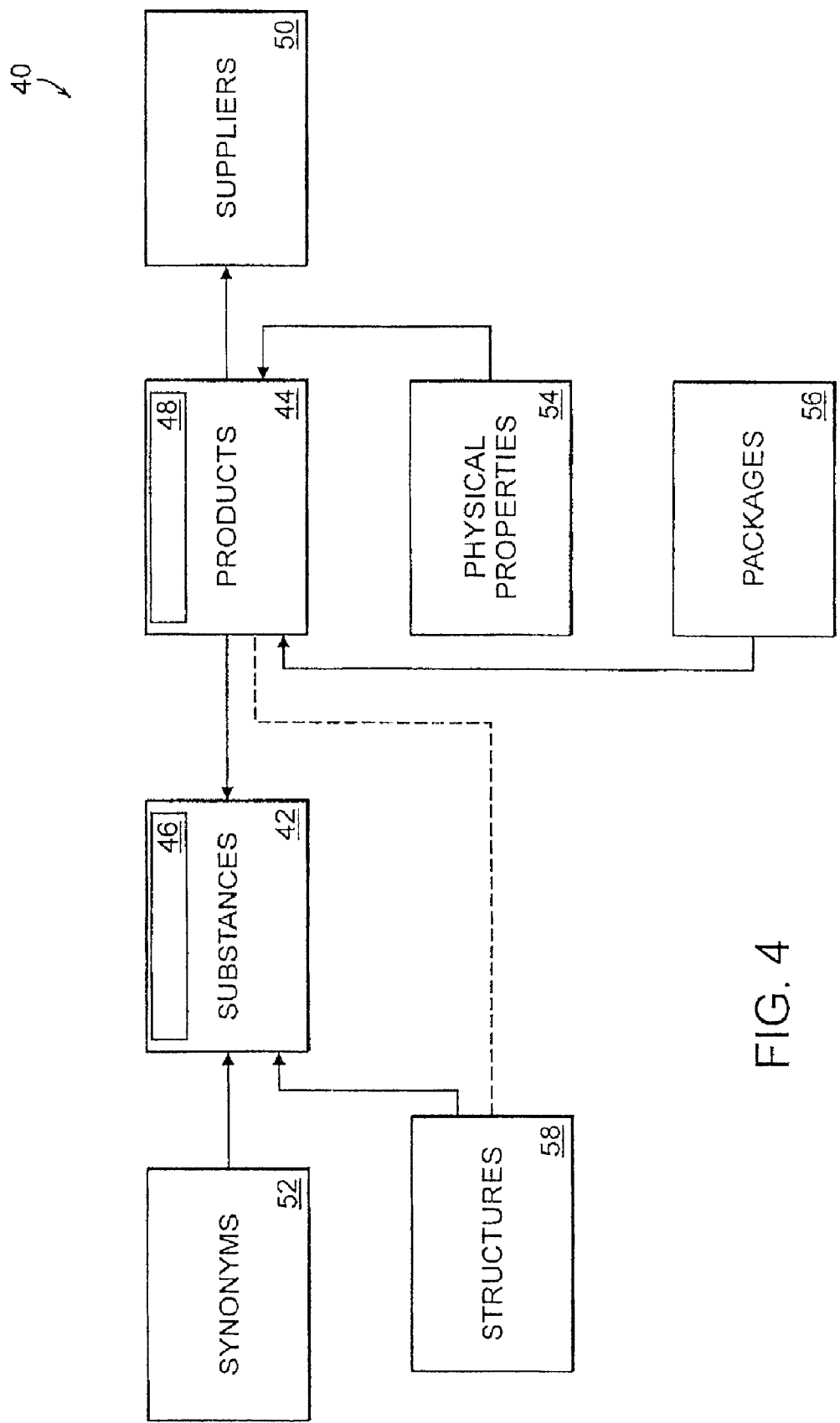

FIG. 4 illustrates a specific embodiment 40 of the standardized products database, in which tables are organized as follows. A substances table 42 and a products table 44 include a substance entry (e.g., entry 46) and a product entry (e.g., entry 48), respectively, for each chemical substance and individual product, respectively, recorded in the database. In embodiment 40, substance entries are linked to product entries in a "one to many" relationship, signified by an arrow from the products table to the substances table in FIG. 4. With this one to many relationship, a single substance entry may be linked to multiple product entries, but a single product entry is linked to only one substance entry. For example, the substances table may have a single entry for salt, which entry is linked to multiple entries in the products table, for salt products in different containers and from different manufacturers.

One to many relationships are also provided between a suppliers table 50 and products table 44, between substances table 42 and a synonyms table 52, between products table 44 and a physical properties table 54, between the products table and a packages table 56, and between substances table 42 and a structures table 58. The suppliers table records identities of product suppliers such as chemical companies. The synonyms table records different names such as "salt" and "sodium chloride" for the same substance. The physical properties table records physical properties such as melting and boiling points for products. The packages table records different packages such as 10 milliliter bottles and 20 gallon barrels in which products may be provided. The structures table records information regarding structural images for substances.

Figure 12:
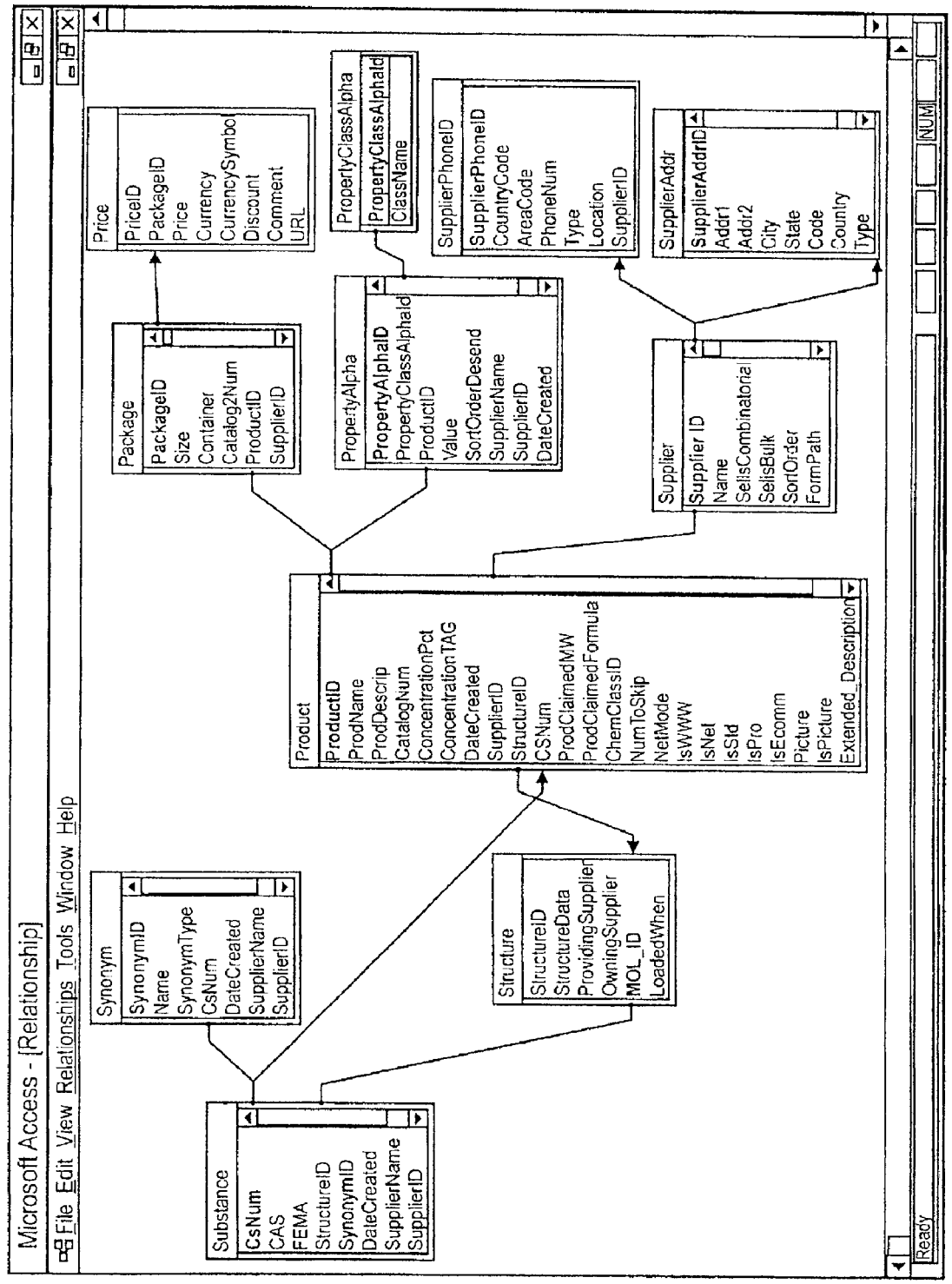

FIG. 12 illustrates a specific example of a relationship table for a standardized products database. FIGS. 13A-13B list database fields of the specific example and demonstrate data types and sample contents of the database fields.

Although a chemical substance has only one chemical structure, the structure can be presented in different views, from different angles, and with emphasis on different features of the structure. A product entry corresponding to a product that is associated with a particular structural representation in a supplier's catalog may also be linked to an entry in the structures table for that representation so that a report derived from the product entry can identify the representation as having originated in the catalog.

Similarly, although a chemical substance has only one set of physical properties, the properties may be expressed differently in different suppliers' catalogs. Thus, in the specific implementation described above, to avoid associating one supplier's product with another supplier's expression of the physical properties for the corresponding substance, entries in the physical properties table are linked to entries in the products table, not to entries in the substances table. Accordingly, a report derived from a product entry can describe the physical properties for the corresponding product as the physical properties were expressed in the catalog.

In at least some cases, it may be advantageous to combine multiple catalog spreadsheet files into one catalog spreadsheet file that is used to supply information to the database. For example, a supplier may provide one spreadsheet that provides information about some characteristics for certain products and another spreadsheet that provides information about other characteristics for the same products. In such a case, the combined spreadsheet file is created by determining, for each row in the first spreadsheet file, the row in the other spreadsheet file that pertains to the same product, and creating a new row having columns that include information from both rows. As described in more detail below in connection with populating the database, two sets of product information may be determined to pertain to the same product if a comparison of information in designated product identification portions of each set indicates a match.

In another example, one spreadsheet file may include information about characteristics for one category of products, such as reagents, and another spreadsheet may include information about characteristics for another category of products, such as aromatics. In such a case, the combined spreadsheet file may be created by concatenating the sets of rows of the spreadsheets.

FIG. 5 illustrates an example 60 of a row of a catalog spreadsheet file. An item number "22" is included in a catalog item number column 62, a product name "Baking soda, bakery grade" is included in a product name column 64, a chemical name "sodium bicarbonate" is included in a chemical name column 66, a CAS number "Z9999999" is included in a CAS number column 68, a supplier number "319" is included in a supplier column 70, a package type number "555" for a 10 milliliter bottle is included in a package type column 72, a structure pointer is included in a structure column 74, and a price value "7.20" is included in a price column 76. Alternatively, in a case in which the spreadsheet file describes products from only one supplier, the spreadsheet file may not include a supplier column, and the supplier number may be acquired by searching the spreadsheet file for an identification of the supplier, such as the supplier's name in a heading, or by prompting the end user as described below in connection with selecting sources.

Figure 6:
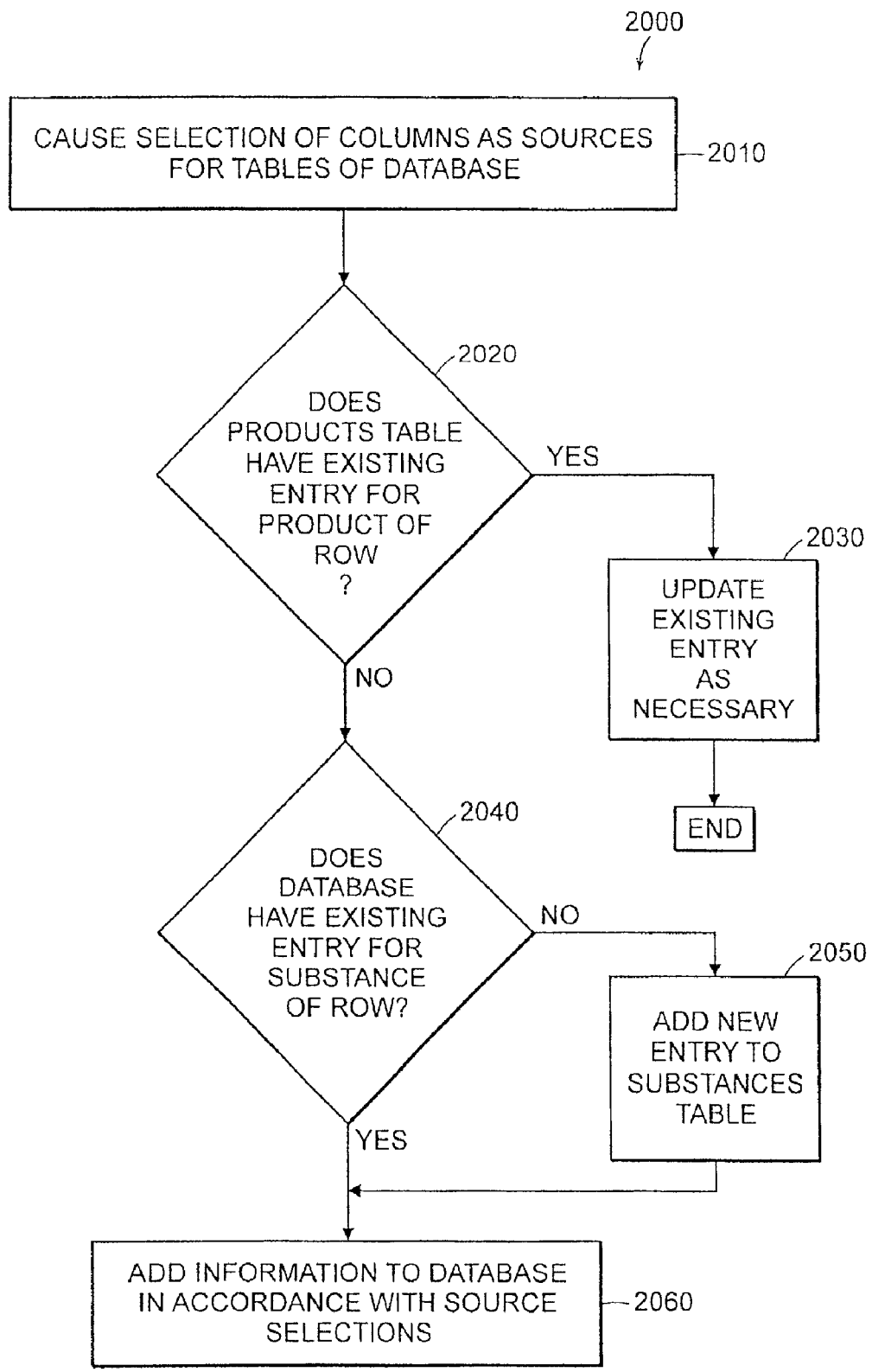

In a specific implementation, information from the row of example 60 is processed according to procedure 2000 (FIG. 6). An end-user is prompted, by use of an input form such as form 80 of FIG. 8, to select columns as sources for the tables of the database (step 2010). The catalog item number column is a suitable source for the products table. The CAS number column is a suitable source for the substances table. The supplier column is a suitable source for the suppliers table. The package type column is a suitable source for the packages table. The structure column is a suitable source for the structures table. The product name, chemical name, and CAS number columns are suitable sources for the synonyms table. If a price table stores a product's price, the price column is a suitable source for the price table. In a case in which the catalog spreadsheet file includes physical property information (e.g., in one or more physical properties columns or in other columns), the location of such information is a suitable source for the physical properties table.

It is determined whether the products table has an existing entry for the product in the row (step 2020). Such a determination may be accomplished by searching the products table and the suppliers table to determine whether the products table has an existing entry that has the same item number as the product and is linked to an existing entry in the suppliers table that has the same supplier number as the product. If the products table does have an existing entry for the product, the existing entry is updated as necessary with the information in the row, e.g., by adding the latest price, or by linking the existing entry to a new structures table entry that includes the row's structure pointer (step 2030).

Otherwise, it is determined whether the database already has one or more existing entries for the substance indicated in the row (step 2040). Such a determination may be made by searching the substances table and the synonyms table to determine whether either table has an existing entry that matches the CAS number, product name, or chemical name provided in the row, and by searching the structures table for an existing pointer to a structure that matches the structure referenced by the structure pointer in the row. Structure matching is performed by software such as ChemFinder® of CambridgeSoft Corporation, Cambridge, Mass.

If no such existing entries are found, a new entry is added to the substances table, and serves as an existing substances table entry for the remainder of procedure 2000 (step 2050). In the case of example 60, the new substances table entry includes CAS number "Z9999999". In a case in which the row includes a structure pointer but does not include a CAS number, the CAS number for the new entry may be acquired by submitting the structure pointer to software such as the ChemFinder® software referenced above.

Information in the row is added to the database in accordance with the source selections provided by the end-user (step 2060). With respect to example 60, a new entry that includes item number "22" is added to the products table and is linked to the existing substances table entry. In addition, entries in the synonyms table that include product name "Baking soda, bakery grade", chemical name "sodium bicarbonate", and the CAS number are added if such entries do not exist already. These entries are linked to the existing substances table entry. An entry in the structures table that includes the row's structure pointer is added if such an entry does not exist already, and is linked to the existing substances table entry. Further, entries in the suppliers table, packages table, and price table that include supplier number "319", package type number "555", and price value "7.20", respectively, are added if such entries do not exist already, and are linked to the new products table entry.

It can be particularly advantageous to help prevent certain errors from entering the database. For example, the use of an erroneous CAS number may result in a single substances table entry being linked to products that in fact are for two different substances. During the transfer of the information from the row to the database, the information may be evaluated. For example, if the CAS number provided in the row conforms to a conventional format in which the CAS number is divided by "-" characters into three sections, the rightmost section is interpreted according to the convention as a checksum, and the checksum is tested against the rest of the CAS number. If the test of the CAS number indicates a problem, the row may be treated as lacking a CAS number.

Figure 9:
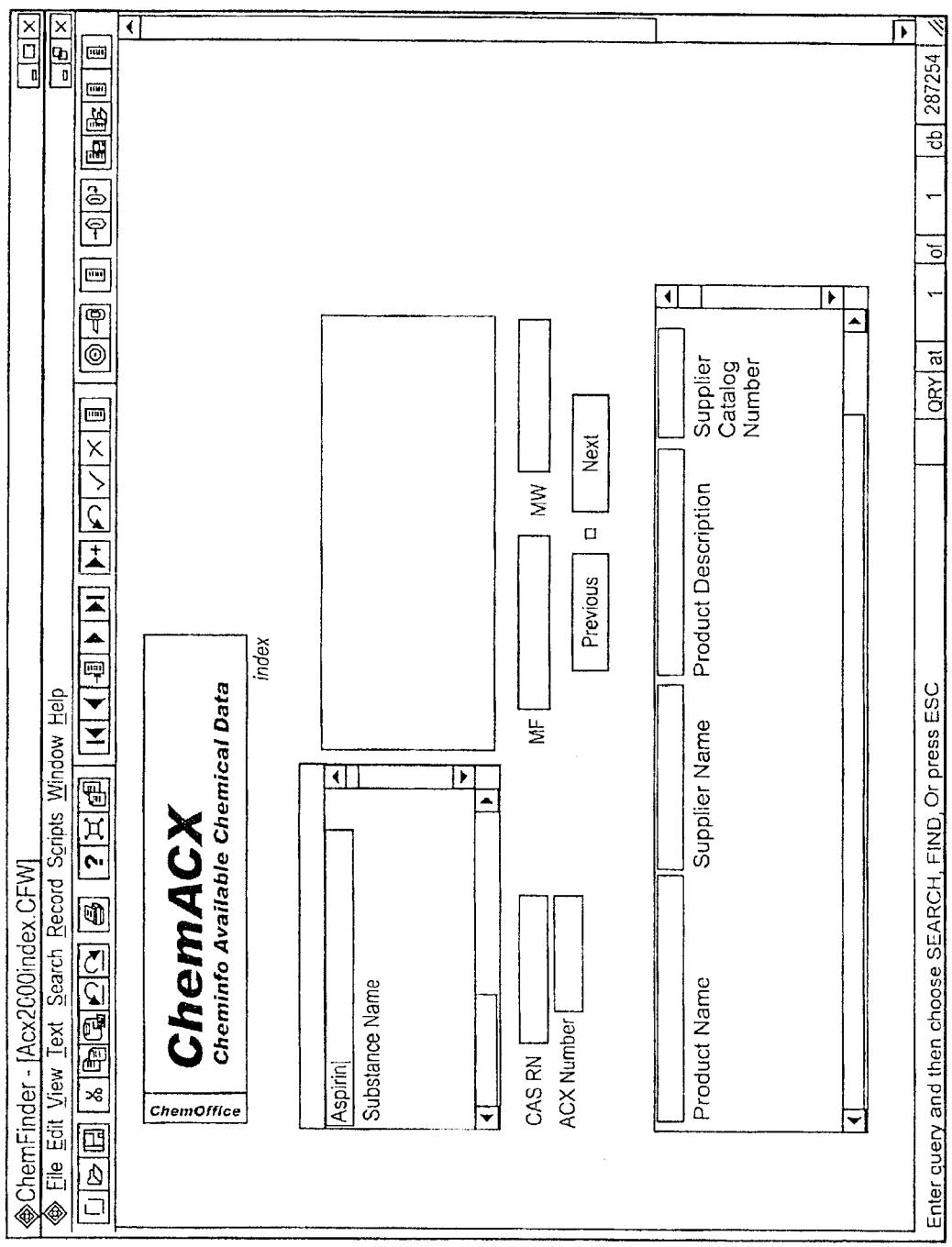
Figure 10:
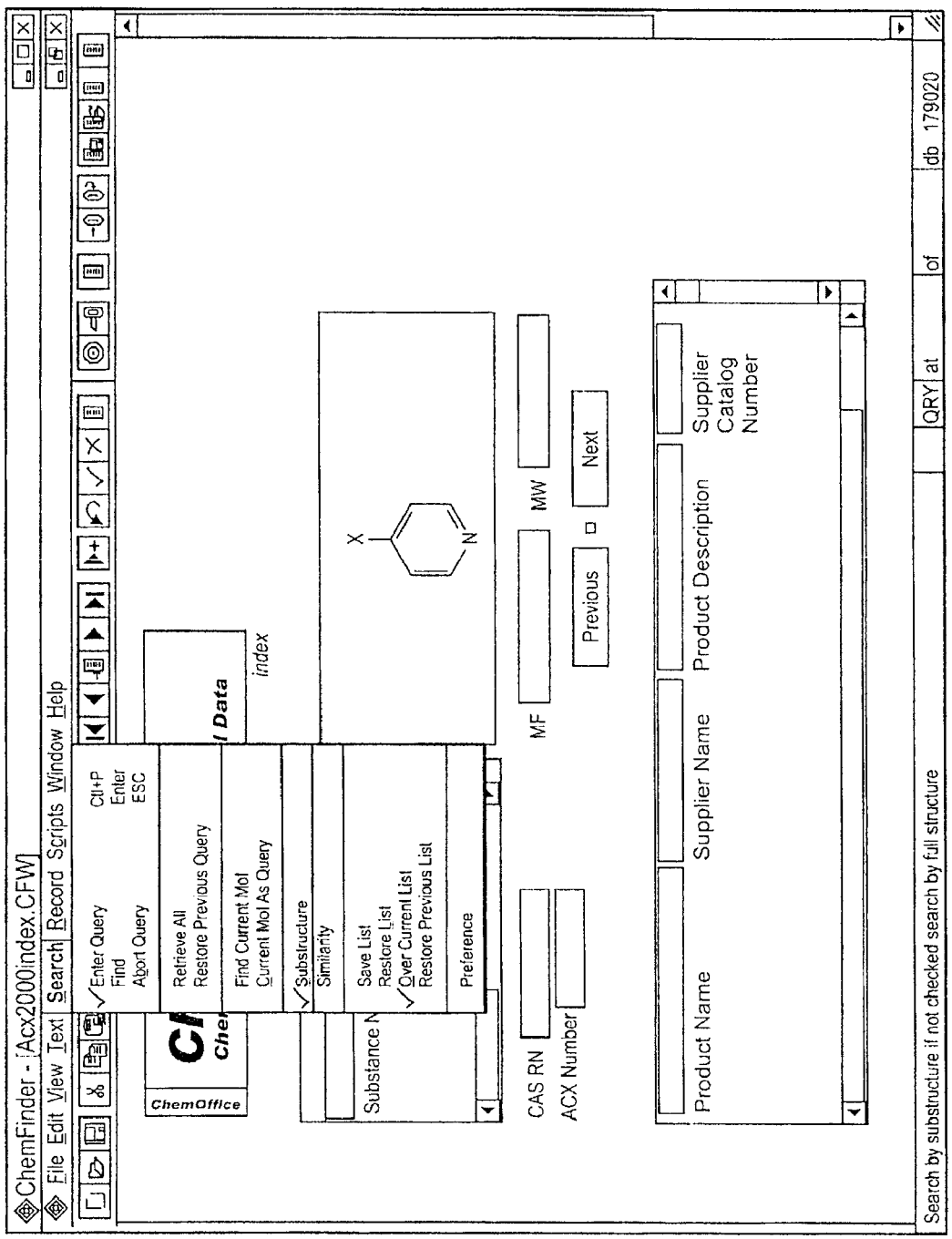
Figure 11:
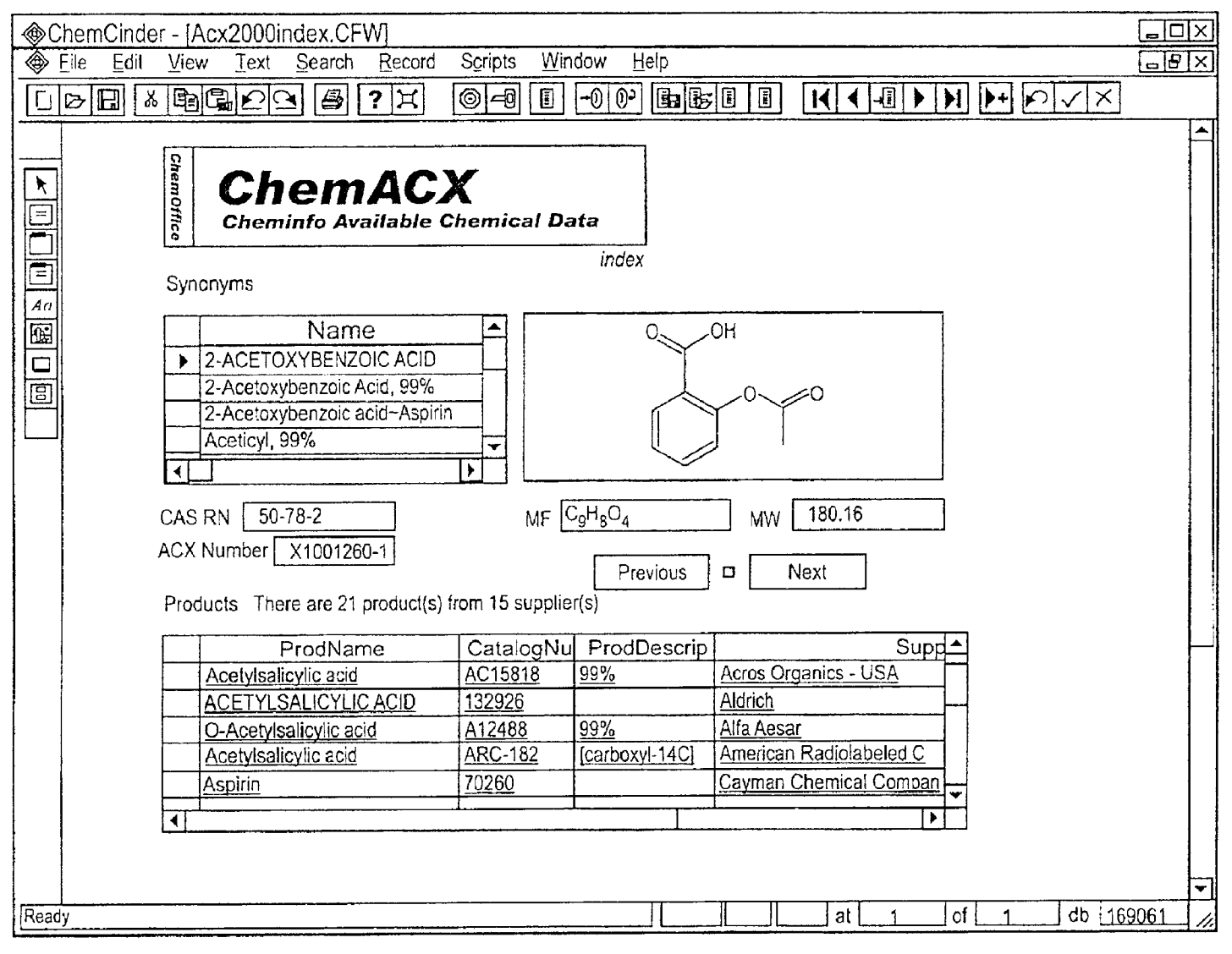

The database allows an end user such as a purchasing agent to search for products by reference to any information in any of the tables. For example, the end user can cause a report to be derived from the database that lists a specific product, or all of the recorded products for any of the recorded suppliers or for any of the recorded substances, together with pertinent chemical structure images. FIGS. 9 and 10 illustrate examples of initiating searches by text and structure, respectively. FIG. 11 illustrates an example of results of the search of FIG. 9.

In particular, in at least some cases as described below, the database allows an end user to determine whether any of the recorded products is an acceptable substitute for specified product, e.g., due to a similar price or the same package type.

In at least some cases, if a spreadsheet file is compliant with Microsoft Excel, execution of a database emulation feature of an instance of Microsoft Excel may be initiated so that the information in the spreadsheet file can be accessed much as database information is accessed. According to the database emulation feature, each row of the spreadsheet is interpreted as a record and the column entries are interpreted as fields of the record.

An end user such as a scientist who is in search of a particular substance may start with a listing derived from the substances table, and then may produce a report indicating suppliers that supply one of the substances in the listing, and then may produce a report showing products by one of the suppliers of the substance.

Figure 8:
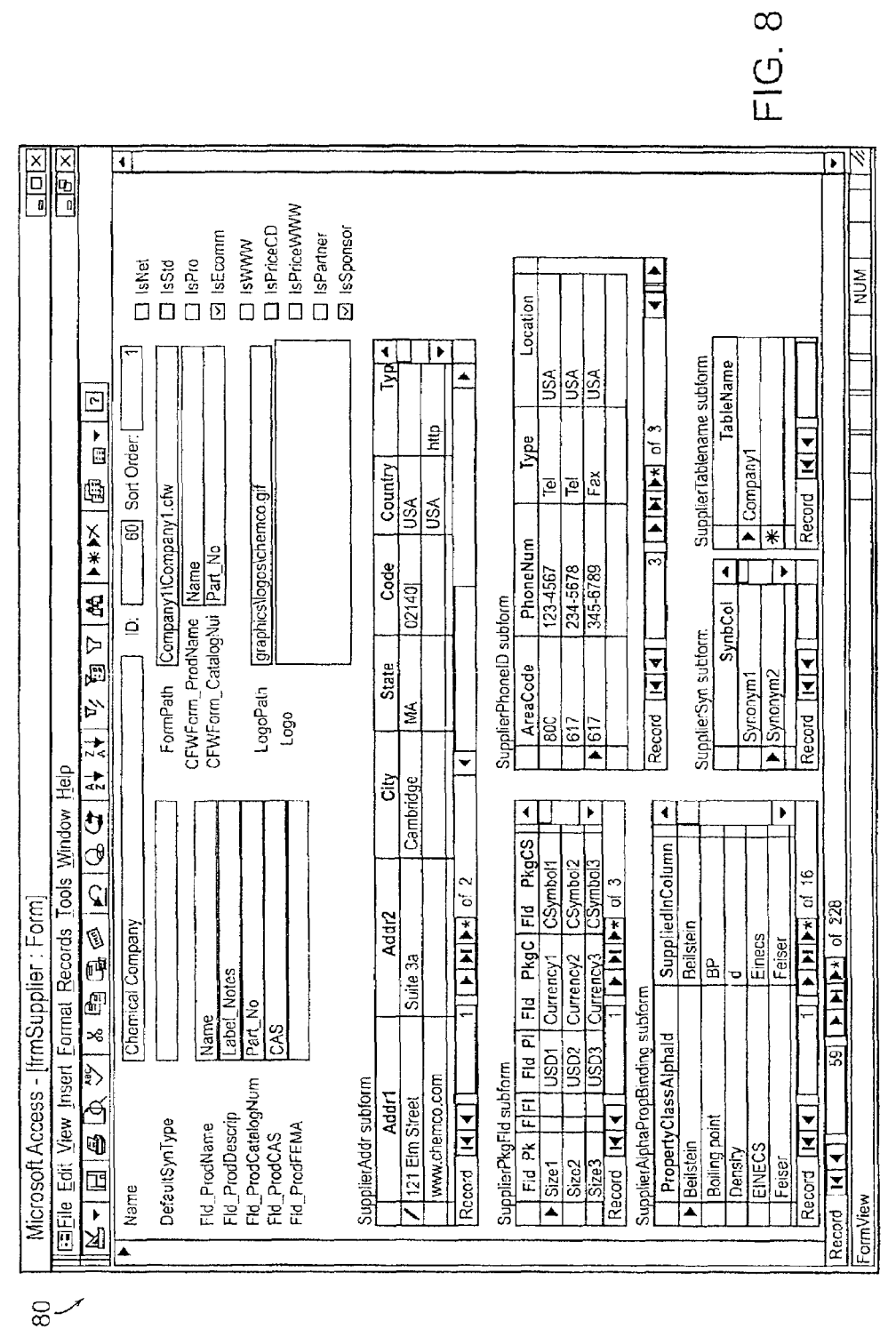

FIG. 8 illustrates a user interface that allow an end user to interact with the spreadsheet and the database.

Figure 7:
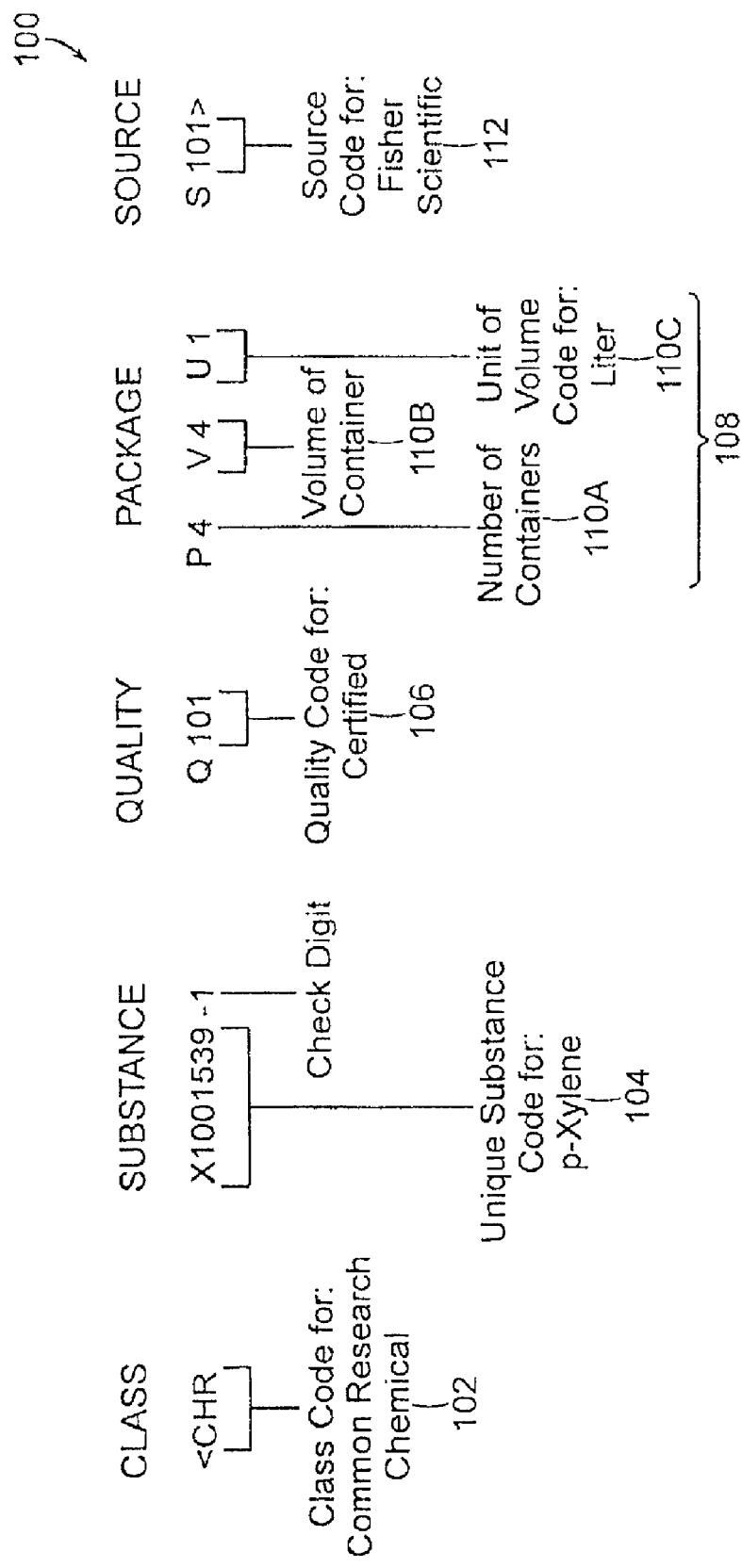

A product identifier ("ACX number") such as number 100 (FIG. 7) may be derived by categorizing products recorded in the database into sets. With reference to FIG. 7, an ACX number for a product has sections that are now described. A class code section 102 indicates the class of substance of the product (e.g., common research chemical). A substance code section 104 identifies a specific substance (e.g., sodium bicarbonate) within the class. A quality code section 106 indicates a level of quality (e.g., 99% pure) of the product. A package code section 108 indicates, in subsections 110A, 110B, 110C, a number of containers included in the product (e.g., four containers in a multipack), a number of units of volume of each container, and the unit of volume (e.g., liter) used, respectively. A source code section 112 identifies the source (e.g., manufacturer) of the product.

The quality code, package code, and source code sections provide information that is not supplied by a CAS number, which identifies a substance only. The ACX number is arranged so that, in at least some cases, the sections are in decreasing left to right order of importance to the consumer, particularly a research scientist. For example, the research scientist may need a particular chemical substance for a chemical reaction, and may need the substance to have at least a certain purity level so that the chemical reaction is not rendered ineffective by impurities. In such a case, the research scientist may desire a particular amount (i.e., volume) of the research chemical, but can accept a larger amount (provided that the excess can be discarded) and may be able to make use of a smaller amount, by reducing proportionately the amounts of other substances to be used in the reaction. With respect to the source code section, the research scientist may not have a significant concern regarding the identity of the supplier or manufacturer.

A specific implementation has the following characteristics. Substances and suppliers that are recorded in the database are assigned respective substance and source codes sequentially. Products are categorized into multiple quality categories, with each category assigned a respective quality code. The categorization may be accomplished by acquiring quality description information from the product names in the database tables (e.g., "bakery grade" from a product name "baking soda, bakery grade", or "98% purity" from "sodium bicarbonate, 98% purity") and analyzing the quality description information to determine the appropriate category for each product. (Alternatively, the quality description information may be acquired from spreadsheet rows, particularly the product name column, as the information in the rows is being copied to the database.) Example quality categories include "reagent grade", "assay grade", "HPLC grade", and ranges of purities such as 90% to 93%. Quality description information may be normalized to a common standard, so that, for example, a quantity value of "1 liter" is normalized to "1000 ml".

Numerical quality information may rounded, so that, for example, a purity value of 95.3% may be rounded to 95%. In a specific implementation, textual quality information may be converted to numerical quality information, so that, for example, "reagent grade" is converted to a purity range of 99% to 100%. Quality categories may be arranged to overlap, so that a wide range quality category may be specified to indicate the acceptability of any product that belongs to a narrow range category that falls within the wide range quality category.

ACX numbers, or appropriate adaptations, may be used for products other than research chemicals, such as other products that are used in a laboratory. For example, test tubes may be described in terms of quality (e.g., "plastic", "rubber", or "glass", or a value indicating a level of resistance to reacting with the contents), number of items in the product (e.g., 24 test tubes to a box), volume of each test tube, and the unit of volume used, as described above.

A physical mixture may be described by an ACX number or an appropriate adaptation. For example, a particular toothpaste product may have an ACX number that may be used to refer to a set of other ACX numbers representing products that make up the ingredients of the toothpaste product.

A variation of the ACX number format may be used to indicate a research chemical's characteristics with respect to cross reactions. Such a variation may be particularly useful with medical or pharmaceutical substances. For example, a first topical substance may react with a second topical substance to create a third substance that is harmful to a patient. In such a case, tracking the chemical's cross-reactions can help to avoid causing problems.

An ACX number may be used in any situation in which the application of a compact, meaningful description of a product would be advantageous. For example, a research chemical product may be labeled with the ACX number so that a research scientist using the product can specify the product by the ACX number. A purchasing agent is thereby provided with information that, in many cases, is sufficient by itself to allow the purchasing agent to find an acceptable substitute for the specified product, because any product having an ACX number that precisely matches all but the source code section of the specified ACX number is highly likely to serve the needs of the research scientist. In addition, any product having an ACX number that precisely matches all but the source code and package code sections of the specified ACX number is highly likely to serve the needs of the research scientist, albeit possibly with some adjustments to account for quantity and package style differences.

An ACX number may be used in an electronic commerce environment so that a computer programmed to compare ACX numbers can readily identify a research chemical product or other product that is an acceptable substitute for a specified product, and report such identifications to an end-user. In a specific embodiment, each product recorded in the standardized products database described above may be assigned a respective ACX number, which may be recorded in the products table. In such a case, whenever a recorded product is listed, the corresponding ACX number may be displayed to facilitate an end-user's search for acceptable substitutes.

An on-line registration process may be provided so that a new product may be assigned an ACX and recorded in the standardized products database. For example, a Web page may be provided that accepts product information, perhaps including addresses of relevant on-line Web pages or other information. In such a case, the ACX number may be determined by analyzing the product information to determine, among other things, whether the database has an existing entry and therefore an existing substance code for the substance of the product. After being determined, the ACX number may be reported by electronic mail to the initiator (e.g., end user) of the registration of the product.

ACX numbers may also be used to track products such as chemicals throughout an organization, including in inventory and in recording reactions in reactions notebooks or databases.

Documents such as research papers and articles that include ACX numbers can be indexed by ACX number so that, for example, documents that refer to a particular product can be reliably listed and retrieved. In the case of Web pages and other electronic documents, ACX numbers can be embedded and linked so that selecting the ACX numbers, e.g., with mouse clicks, causes the display of information that is relevant to the product or to a feature of the product, such as the substance of the product.

All, or a portion of the procedures described above may be implemented in hardware or software, or a combination of both. In at least some cases, it is advantageous if the technique is implemented in computer programs executing on one or more programmable computers, such as a personal computer running or able to run an operating system such as Unix, Linux, Microsoft Windows 95, 98, 2000, or NT, or MacIntosh OS, that each include a processor, a storage medium readable by the processor (including volatile and non-volatile memory and/or storage elements), at least one input device such as a keyboard, and at least one output device. Program code is applied to data entered using the input device to perform the technique described above and to generate output information. The output information is applied to one or more output devices such as a display screen of the computer.

In at least some cases, it is advantageous if each program is implemented in a high level procedural or object-oriented programming language such as Perl, C, C++, or Java to communicate with a computer system. However, the programs can be implemented in assembly or machine language, if desired. In any case, the language may be a compiled or interpreted language.

In at least some cases, it is advantageous if each such computer program is stored on a storage medium or device, such as ROM or optical or magnetic disc, that is readable by a general or special purpose programmable computer for configuring and operating the computer when the storage medium or device is read by the computer to perform the procedures described in this document. The system may also be considered to be implemented as a computer-readable storage medium, configured with a computer program, where the storage medium so configured causes a computer to operate in a specific and predefined manner.

Other embodiments are within the scope of the following claims. For example, the columns that are to serve as sources for the tables may be selected fully or partially automatically, perhaps by a process that analyzes the contents of column headers to determine the type of information that is provided in the column. The ACX number may be provided in a form that is particularly suitable for detection or interpretation by a computer, such as in a bar code format or encoded on a magnetic strip.

What is claimed is:

1. A computer-implemented method for use in managing product information, comprising:
    downloading product information from an electronic catalog, the product information being readable by a computer;
    determining that the product information includes a product identifier and chemical structure information that is associated with the product identifier;
    deriving a product descriptor string from the product information, the product descriptor string being readable by a computer, the product descriptor string comprising:
        a first string section identifying a chemical substance corresponding to the chemical structural information; and
        a second string section having quality description information of a product identified by the product identifier;
    identifying a desired product having a chemical structure and a quality description; and
    presenting information that communicates at least one product having substantially the same chemical structure and quality description as the desired product based on at least the first string section and the second string section of the product descriptor string of the desired product.

2. The method of claim 1, further comprising:
    storing the product identifier and the chemical structure information in a database of chemical product information, with the product identifier linked to the chemical structure information.

3. The method of claim 1, further comprising:
    determining that the product information includes a product identifier and physical property information that is associated with the product identifier; and
    storing the product identifier and the physical property information in the database with the product identifier linked to the physical property information.

4. A computer-implemented method for use in managing product information, comprising:
    downloading product information for a chemical product, the product information being readable by a computer;
    deriving, from the product information, a substance identifier for the chemical product;

deriving, from the product information, a quality identifier for the chemical product;
deriving a product descriptor string from the substance identifier and the quality identifier, the product descriptor string being readable by a computer, the product descriptor string comprising:
  a first string section identifying a chemical substance corresponding to the substance identifier; and
  a second string section having quality description information corresponding to the quality identifier;
identifying a desired product, the desired product comprising a desired chemical substance and the desired product having a quality description; and
presenting information that communicates at least one product of substantially the same chemical substance and having substantially the same quality description as the desired product based on at least the first string section and the second string section of the product descriptor string of the desired product.

5. The method of claim 4, further comprising:
determining, from the product information, a quality category to which the chemical product belongs.

6. The method of claim 5, wherein the determination comprises interpreting the quality identifier.

7. The method of claim 4, further comprising:
determining, from the product information, whether the chemical product has a purity that matches specified purity criteria.

8. The method of claim 7, wherein the determination comprises interpreting the quality identifier.

9. The method of claim 4, further comprising:
determining, from the product information, whether the chemical product is of a specified grade of chemical products.

10. The method of claim 9, wherein the determination comprises interpreting the quality identifier.

11. The method of claim 4, further comprising:
deriving, from the product information, a quality value in a predetermined format.

12. The method of claim 4, further comprising:
arranging sections of the product identifier according to an order of importance to a consumer of the chemical product.

13. The method of claim 4, further comprising:
providing the product identifier with a section that indicates only the source of the chemical product.

14. The method of claim 13, further comprising:
providing the product identifier with another section that indicates only the package style of the chemical product.

15. A system for use in managing product information, comprising:
  a downloading mechanism downloading product information from an electronic catalog, the product information being readable by a computer;
  a determiner determining that the product information includes a product identifier and chemical structure information that is associated with the product identifier;
  a deriver deriving a product descriptor string from the product information, the product descriptor string being readable by a computer, the product descriptor string comprising:
    a first string section identifying a chemical substance corresponding to the chemical structural information; and
    a second string section having quality description information of a product identified by the product identifier;
  an identification mechanism identifying a desired product having a chemical structure and a quality description; and
  a presenting mechanism presenting information that communicates at least one product having substantially the same chemical structure and quality description as the desired product based on at least the first string section and the second string section of the product descriptor string of the desired product.

16. A system for use in managing product information, comprising:
  a downloading mechanism downloading product information for a chemical product, the product information being readable by a computer;
  a deriver:
    deriving, from the product information, a substance identifier for the chemical product;
    deriving, from the product information, a quality identifier for the chemical product; and
    deriving a product descriptor string from the substance identifier and the quality identifier, the product descriptor string being readable by a computer, the product descriptor string comprising:
      a first string section identifying a chemical substance corresponding to the substance identifier; and
      a second string section having quality description information corresponding to the quality identifier;
  an identifying mechanism identifying a desired product, the desired product comprising a desired chemical substance and the desired product having a quality description; and
  a presenting mechanism presenting information that communicates at least one product of substantially the same chemical substance and having substantially the same quality description as the desired product based on at least the first string section and the second string section of the product descriptor string of the desired product.

17. A computer-implemented method for use in managing product information, comprising:
  querying a database of products, the database containing one or more fields for a product descriptor string, the product descriptor string being associated with a corresponding product, the product descriptor string comprising:
    a first string section identifying a chemical substance of the product associated with the product descriptor string; and
    a second string section having quality description information of the product associated with the product descriptor string;
  in response to querying the database, selecting at least one product having substantially the same chemical substance and quality description as a desired product based on at least the first string section and second string section of the product descriptor string of the desired product; and
  presenting information that communicates the at least one product having substantially the same chemical substance and quality description as a desired product.

18. The method of claim 17, the database further containing chemical structure information associated with at least one product.

19. The method of claim 17, the database further containing physical property information associated with at least one product.

20. The method of claim 17, wherein the quality description information includes a product purity.

21. The method of claim 17, wherein the quality description information includes a specified grade of chemical products.

22. The method of claim 17, each of said product descriptor strings further comprising a third string section indicating a source of the product associated with the product descriptor string.

23. The method of claim 22, each of said product descriptor strings further comprising a fourth string section indicating a package style of the product associated with the product descriptor string.

* * * * *